(12) United States Patent
Hibbs et al.

(10) Patent No.: US 8,283,157 B2
(45) Date of Patent: Oct. 9, 2012

(54) SYSTEM AND METHOD FOR INCREASING POLYMER/NANOPORE INTERACTIONS

(75) Inventors: Andrew D Hibbs, La Jolla, CA (US); Geoffrey Alden Barrall, San Diego, CA (US); Eric N Ervin, Park City, UT (US); Daniel K Lathrop, San Diego, CA (US)

(73) Assignee: Electronics Biosciences, Inc., San Diego, CA (US)

( * ) Notice: Subject to any disclaimer, the term of this patent is extended or adjusted under 35 U.S.C. 154(b) by 0 days.

(21) Appl. No.: 12/999,157

(22) PCT Filed: Jun. 18, 2009

(86) PCT No.: PCT/US2009/047804
§ 371 (c)(1),
(2), (4) Date: Dec. 15, 2010

(87) PCT Pub. No.: WO2009/155423
PCT Pub. Date: Dec. 23, 2009

(65) Prior Publication Data
US 2011/0162963 A1    Jul. 7, 2011

Related U.S. Application Data

(60) Provisional application No. 61/073,668, filed on Jun. 18, 2008.

(51) Int. Cl.
*C12M 1/00*    (2006.01)

(52) U.S. Cl. ............... 435/287.2; 204/451; 204/601
(58) Field of Classification Search .......... 204/450–453, 204/518, 600–604, 627; 435/287.2, 288.2, 435/288.6, 50, 68.1, 99; 977/963
See application file for complete search history.

(56) References Cited

U.S. PATENT DOCUMENTS

| | | | |
|---|---|---|---|
| 6,746,594 B2 | 6/2004 | Akeson et al. | |
| 6,955,670 B2 | 10/2005 | Martin et al. | |
| 2004/0106190 A1 | 6/2004 | Yang et al. | |
| 2005/0014162 A1* | 1/2005 | Barth et al. | 435/6 |
| 2005/0186629 A1* | 8/2005 | Barth | 435/6 |
| 2008/0041733 A1 | 2/2008 | Hibbs et al. | |

* cited by examiner

*Primary Examiner* — J. Christopher Ball
(74) *Attorney, Agent, or Firm* — Diederiks & Whitelaw, PLC (57) ABSTRACT

An electrolytic system includes an analyte chamber having an access port for introducing a sample containing a molecules of interest, such as DNA. Electrodes create an electric field along a length of the analyte chamber to drive molecules toward an interaction region containing a nanopore, thereby increasing the arrival rate of molecules at the nanopore. Additional electrodes may be utilized to create an electric field through the nanopore to drive a molecule into the nanopore. A current sensor may be utilized to count, discriminate or characterize the molecules as they interact with the nanopore. Advantageously, system can be utilized for unamplified DNA sequencing.

29 Claims, 8 Drawing Sheets

SYSTEM AND METHOD FOR INCREASING POLYMER/NANOPORE INTERACTIONS

CROSS-REFERENCE TO RELATED APPLICATIONS

This application represents a National Stage application of PCT/US2009/047804 entitled "System and Method for Increasing Polymer/Nanopore Interactions" filed Jun. 18, 2009, pending which claims the benefit of U.S. Provisional Patent Application Ser. No. 61/073,668 entitled "Nanopore-Based System to Sequence Unamplified DNA" filed Jun. 18, 2008.

BACKGROUND OF THE INVENTION

Extensive amounts of research and money are being invested to develop methods to sequence individual strands of DNA. However, in most proposed single molecule sequencing approaches, the overall rate of sequencing is limited by the rate of arrival of individual target molecules at the sequencing element. One way to increase the overall rate of arrival is to amplify the number of DNA molecules in the solution using a polymerase chain reaction or equivalent method. Such amplification is required for all existing DNA sequencing approaches and adds considerable cost and complexity, particularly if an entire human genome is to be amplified. To realize the true potential of such single molecule sequencing methods, the overall measurement approach should ideally not require amplification of the original DNA sample.

For example, a good commercial DNA processing system can extract DNA equivalent to 30 million genomes from 100 µl of blood. A compact nanopore-base measurement system as recently described by Barrall et al., (Barrall et al. 2008, Ervin and Barrall 2007) has an analyte volume of order 50 micro liters (µl), resulting in an average of only 15 million genomes in the sensing volume that contains the nanopore. Scaling from capture rate data of short (~1 kilobase) DNA strands, a capture rate of one target molecule per 80,000 seconds is projected. Thus, unless the number of molecules in the vicinity of the nanopore is somehow increased, a reasonable sample of unamplified DNA would have a single molecule capture rate or nanopore/molecule interaction of order one per day.

Another approach that effectively increases the number of molecules is to reduce the volume of solution in the measurement apparatus while keeping the number of molecules the same. This can be affected by a conventional technique such as centrifuging the sample prior to inserting it into the sequencing apparatus. However, this introduces an additional step into the work flow that adds cost. Furthermore, when the initial number of target molecules is small, such as when collecting a pathogen from the environment, preconcentration has the significant downside of reducing the sample volume to potentially an unacceptable small level. For example, if the starting sample volume is 10 µl then concentrating it by a factor of 1000 would result in a volume of 0.01 µl. Such a sample requires an exceptionally small analyte chamber, requiring advanced fabrication and fluid handling technology.

Furthermore, to achieve an acceptable sequencing throughput, it is expected that an array of nanopores will be required. The present state of technology suggests a nanopore sequencing rate of order 10,000 bases per second. To sequence the 3 billion bases of the human genome in three hours, it would require at least 30 nanopores and likely much more (500 nanopores) if the DNA is broken into smaller sub strands. An array of such pores would require an analyte volume much larger than for a system that contained a single nanopore. Thus, the conventional step in the prior practice of preconcentrating the sample to a smaller volume makes constructing an array of sequencing elements within the same analyte volume all the more challenging.

Generally, the arrival rate of the target molecules at a detection element or nanopore is limited by the diffusion rate of the molecule in solution. A possible solution would thus be to increase the diffusion rate of the target molecules, for example by increasing the temperature of the electrolyte or increasing the molecular mobility. However, such modifications may not be compatible with the method used to identify the molecule, and in particular may be very deleterious. For a more detailed discussion of the problems associated with diffusion of target molecules, see U.S. patent application Ser. No. 12/395,682 entitled "System and Method to Improve Sequencing Accuracy of a Polymer" filed Mar. 1, 2009.

Accordingly, a method is needed to increase the number of target molecules within the vicinity of a nanopore without pre-concentrating the sample, and thereby reducing its volume, and without increasing the absolute number of analyte molecules by molecular amplification. Such a method must be compatible with the constraints imposed by the sensing system and detection element, for example it should not add to the noise level of the sensing system, and must be compatible with the voltage and pressure tolerances of the detection element.

SUMMARY OF THE INVENTION

An electrolytic sensing system of the present invention is utilized for increasing the number of target molecules within the vicinity of a nanopore. A particular application is the measurement of an unamplified polymer, and more specifically, for the sequencing of unamplified DNA. The system includes a long, thin analyte chamber having a nanopore or small number of nanopores formed therein within an interaction region. More specifically, the analyte chamber has a length approximately 100 times the width and height of the chamber, with the interaction region located at a specific distance from the second electrode. A sample including an analyte of interest is introduced into the analyte chamber through an access port. First and second electrodes are positioned on either side of the interaction region and provide an electric field along the length of the analyte chamber. This field causes an electrophoretic force that drives the target molecules or analytes of interest toward the nanopore in order to increase the number of target molecules in the vicinity of the nanopore (i.e., the interaction region) and, thereby, increase the number of molecules per unit time that interact with the nanopore. The analyte of interest may then be measured or analyzed utilizing pore blocking signals detected by a current sensor. The analyte can be any electrically charged molecule, preferably a biopolymer (e.g., DNA) and the measurement is preferably directed to determining the sequence of the polymer. In a preferred embodiment, the invention comprises a method to increase the rate of sequencing, by increasing the rate that individual DNA molecules arrive at the nanopore. Another beneficial feature of the invention is that it allows the volume of analyte needed to be very small (~1 µl). Accordingly, an initial sample (e.g., 100 µl) can be divided into subsamples and dispensed into a number of separate measurement systems, thereby providing the extra throughput of an array without the complexity of integrating the array elements into a single unit.

In some cases it may be preferable to turn off the electrophoretic field while a target analyte is interacting with the nanopore, in order to reduce the noise in the circuit that produces the electrophoretic field from coupling into the nanopore. In that case, the dimensions of the interaction region are preferably chosen so that when the electrophoretic field is turned off, the number of target molecules in the interaction region remains significantly enhanced to cause many interactions with the nanopore before the molecules diffuse back into the analyte chamber. In a first example, single strand DNA molecules of order 100 bases long have a diffusion constant of $10^{-7}$ cm$^2$/s. If such molecules are drawn from an analyte chamber of length 100 μm, the time for the number of molecules to be return to their initial equilibrium value prior to application of the driving field is of order 500 seconds. In contrast, when their number is locally increased in accordance with the invention, such DNA molecules may interact with a nanopore sensing element at the rate of one per second, thereby enabling many interactions while the driving field is turned off.

In some cases, it is desirable that the electrophoretic field be reversed for a short time in order to reverse the net transfer of charge from one electrophoresis electrode to the other in order to extend the lifetime of the electrodes. In such cases, timing and amplitude of the reversed field can be optimized based on the duration of the analyte interaction with the pore and the natural return to equilibrium of the analyte solution.

DETAILED DESCRIPTION OF THE PREFERRED EMBODIMENTS

In general, the present invention is directed to a system and method for increasing the number of target molecules within the vicinity of a nanopore. The molecules can range from single ions to long polymers. The nanopore can be part of a measurement system that detects the molecules, or characterizes them in some way, such as determining their length, mass, composition or counting the number of molecules. In the preferred embodiment, the invention is utilized for the sequencing of unamplified polymers, especially DNA.

Figure 1:
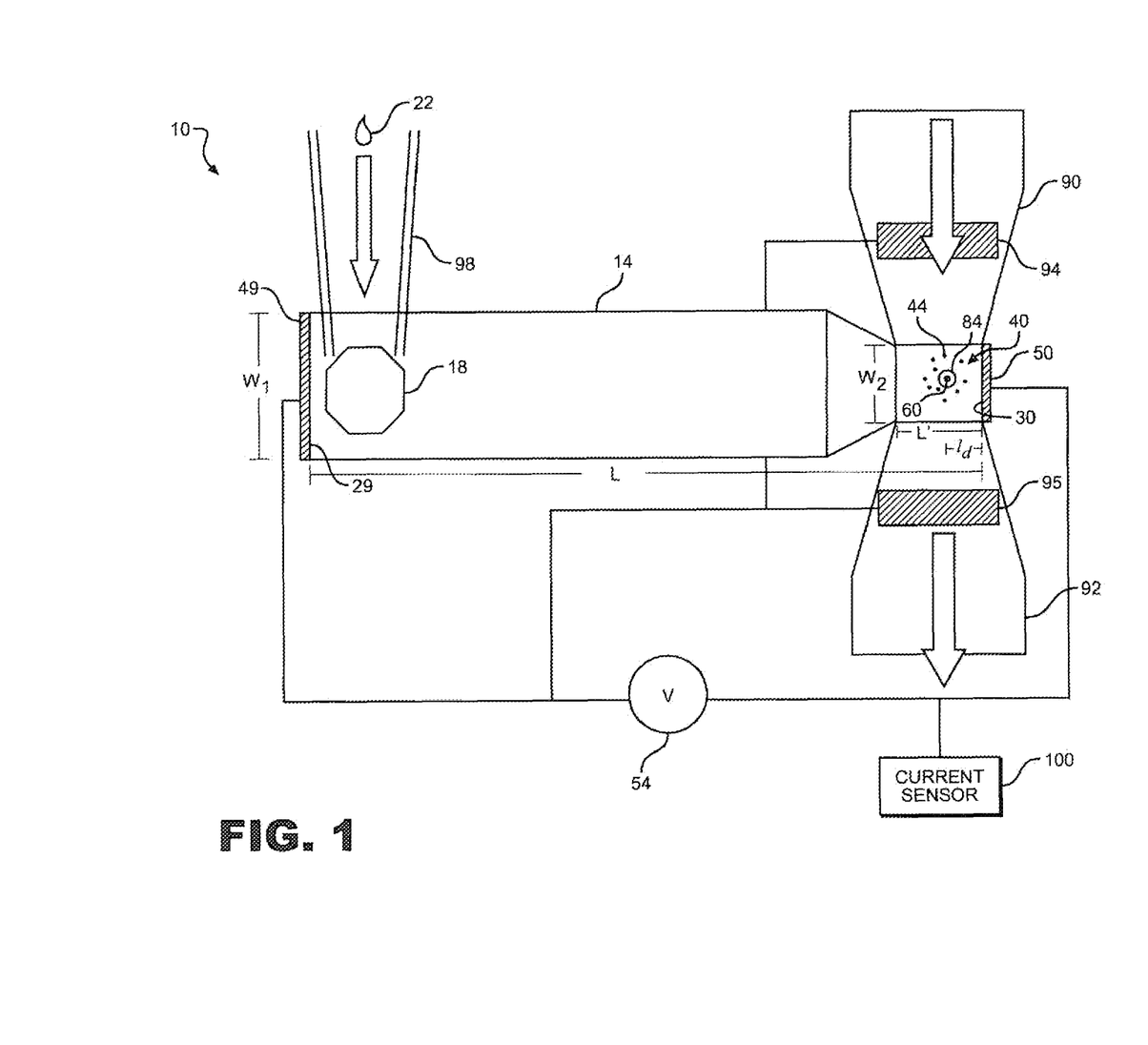
FIG. 1 is a diagram of an electrolytic sensing system for unamplified polymer sequencing in accordance with the present invention.

With reference to FIG. 1, an electrolytic sensing system 10 of the present invention includes a first fluid chamber or analyte chamber 14 including an input port 18. A sample of analyte indicated at 22 containing molecules to be sequenced or otherwise measured may be injected into analyte chamber 14 via input port 18. Analyte chamber 14 is depicted as approximately rectangular in cross section and in end to end geometry consistent with general fabrication methods for microfluidic channels, but can have any shape or cross section. The key geometry property is that it has one dimension much longer than the others. For example, the long axis or length L of analyte chamber 14 defined between a first end 29 and a second end 30 of analyte chamber 14, is generally greater than about 100 micrometers (μm) in length and more preferably greater than about 1 centimeter (cm) in length, while the geometric mean of its height H (depicted in FIG. 4) and width $W_1$ are of order L/100 or less (i.e. about 1 μm-0.01 cm). Analyte chamber 14 includes an interaction region 40 wherein one or more target molecules indicated at 44 accumulate by the action of an applied electrophoretic force. More specifically, first and second driving electrodes 49 and 50 located at respective ends 29 and 30 of analyte chamber 14 are connected to a power or voltage source 54. Electrodes 49 and 50 are exposed to electrolyte or buffer solution in analyte chamber 14 in a manner which provides for a good electrical contact between electrodes 49 and 50 and the electrolyte solution. In use, a voltage is applied across electrodes 49 and 50 by voltage source 54 in order to produce an electric field in analyte chamber 14 to drive target molecules 44 into interaction region 40. In FIG. 1, interaction region 40 is shown located proximal one end 30 of analyte chamber 14 and is shown as tapered. However, interaction region 40 can have the same cross sectional area, or a greater cross sectional area, than analyte chamber 14, and interaction region 40 need not be located at an end of analyte chamber 14. For example, interaction region 40 could be close to the middle of analyte chamber 14, in which case target molecules 44 are driven from both ends 29 and 30 of analyte chamber 14 towards the middle. Additionally, input port 18 is shown at the opposite end 29 of analyte chamber 14 to interaction region 40, but as far as the operation of the invention is concerned, input port 18 can be located anywhere within analyte chamber 14. However, for conceptual clarity, the method of the present invention will be discussed with reference to the embodiment shown in FIG. 1.

Figure 2A:
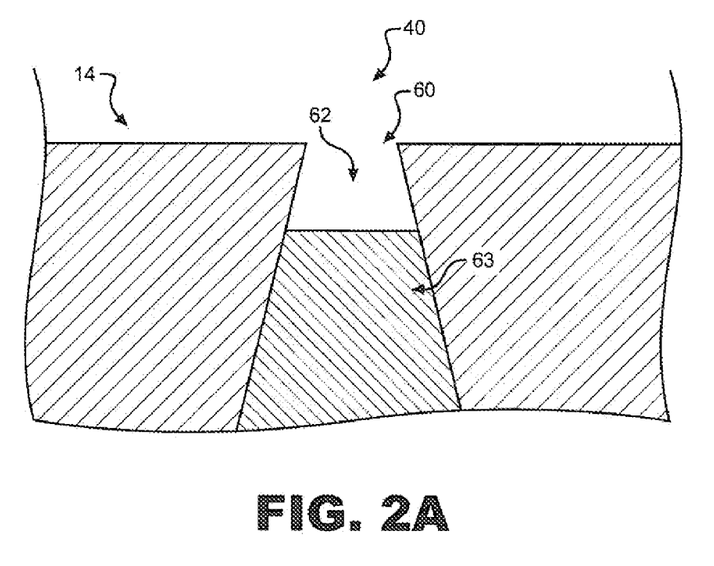
FIG. 2A is a cross-sectional side view of a first nanopore configuration of the present invention.
Figure 2B:
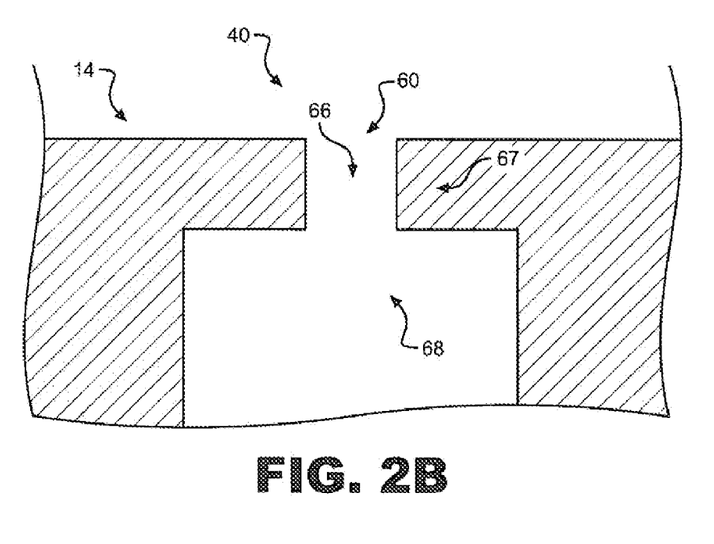
FIG. 2B is cross-sectional side view of an alternate nanopore configuration of the present invention.

In accordance with the invention, at least one nanopore 60 is formed in the analyte chamber 14 within interaction region 40. As depicted in FIG. 2A, nanopore 60 can be comprised of a small volume 62 into which a single target molecule enters and includes some means 63 to interact with the single molecule. More specifically, FIG. 2A depicts a glass nanopore electrode as taught by U.S. patent application Ser. No. 11/744,154 entitled "Nanopore Electrode, Nanopore Membrane, Method of Preparation and Surface Modification, the use thereof", filed May 3, 2007, which is hereby incorporated by reference. More preferably, nanopore 60 comprises a channel 66 spanning a barrier structure 67 separating analyte chamber 14 from a second fluid chamber 68 as shown in FIG. 2B. Each nanopore 60 has an associated volume or capture volume in its immediate vicinity in which an appropriate molecule (i.e., target molecule 44) will interact with nanopore 60 with high probability. Target molecules 44 move within interaction region 40 predominantly stochastically under the process of diffusion until they enter the capture volume of nanopore 60. In general, the purpose of the present invention is to increase the rate target molecules 44 enter the capture volume and interact with nanopore 60 by increasing the number of target molecules 44 within interaction region 40.

The number of nanopores 60 in interaction region 40 is determined by the spacing required between nanopores 60. This spacing is driven by practical system fabrication issues. Increasing the number of nanopores 60 in interaction region 40 increases the number of individual molecules 44 measured per unit time. However, as the size of interaction region 40 is increased to accommodate more nanopores 60, the number of molecules 44 in the capture volume of each nanopore 60 for a given applied voltage will decrease, resulting in a trade-off between increasing the size of interaction region 40 to hold more nanopores 60, and reducing the interaction rate at each nanopore 60.

Figure 3:
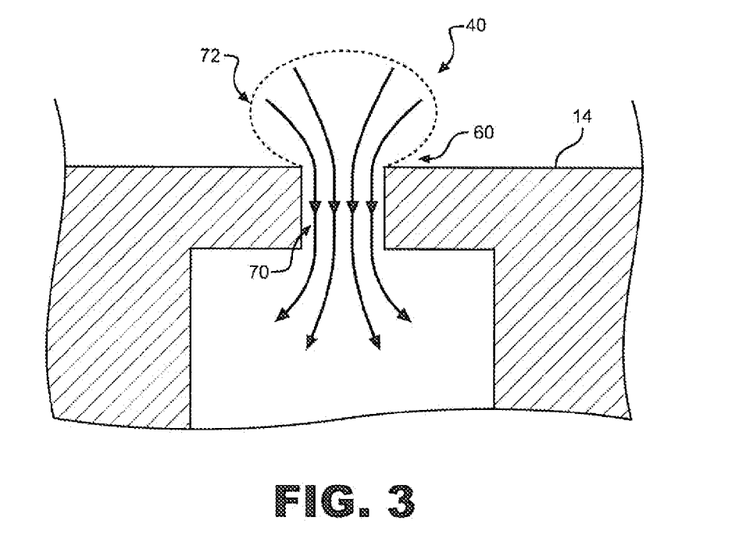
FIG. 3 depicts an electric field in the nanopore of FIG. 2B and in the immediate vicinity of the nanopore opening into the analyte chamber.

Generally, a voltage is applied across nanopore 60 in order to overcome an energy barrier to molecular entry of a target molecule 44 into nanopore 60. Owing to the small size of nanopore 60, the electric field associated with this voltage reaches $10^7$ V/m compared to fields of order $10^3$ V/m or less that can be generated by electrodes 49 and 50 to draw the molecules into interaction region 40. As depicted in FIG. 3, although an electric field 70 is high within nanopore 60, it decreases quickly with distance away from the nanopore opening, having the overall effect of increasing the effective capture volume 72 of nanopore 60 by a factor 10 to 1000 depending on the applied voltage and diffusive properties of the target molecule. The interaction region 40 built according to the invention is a much larger volume into which target molecules 44 are drawn, before being further captured by electric field 70 of nanopore 60.

Figure 4:
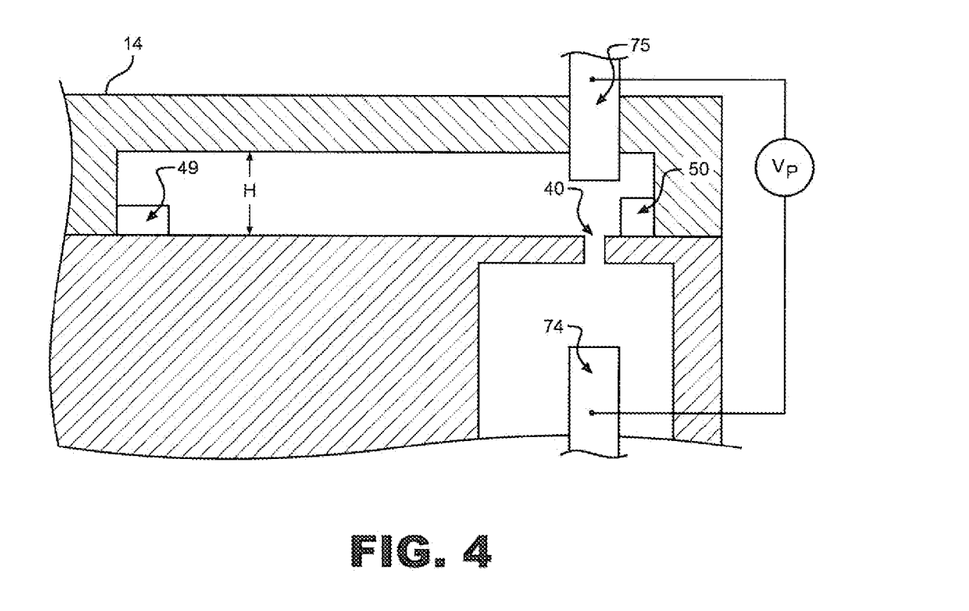
FIG. 4 is a cross-sectional side view of the electrolytic sensing system of claim 1, showing use of an independent set of electrodes to apply a bias voltage across the nanopore.

In use, a voltage difference $V_p$ applied across nanopore 60 to overcome the entry barrier can be produced between an electrode 74 and either of electrodes 49 and 50, as depicted in FIG. 4. Alternatively, a dedicated electrode 75 electrically connected to the electrolyte within interaction region 40 can be provided instead of relying on electrodes 49 or 50. Generally, the electrical circuit across nanopore 60 must be as low noise as possible, which requires the use of larger and more expensive electrodes. Thus, an advantage of providing an independent electrode 75 for the nanopore bias $V_p$ is that each set of electrodes can be optimized for its respective function.

Figure 5A:
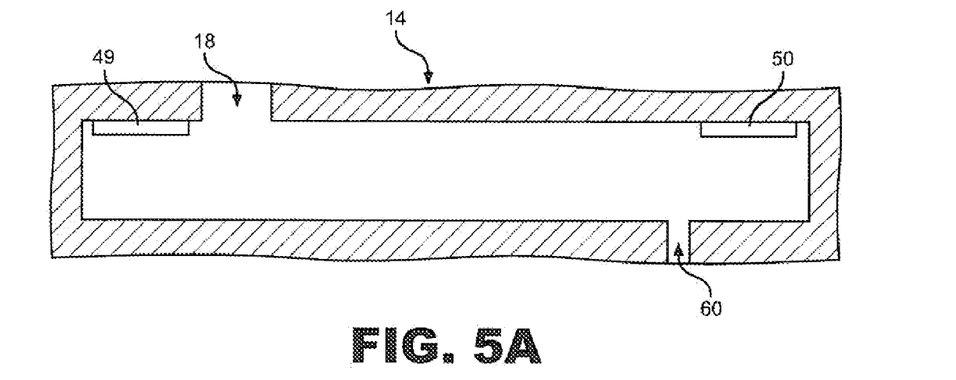
FIG. 5A depicts a first analyte chamber of the present invention including electrodes fabricated on the upper surface of the analyte chamber.
Figure 5B:
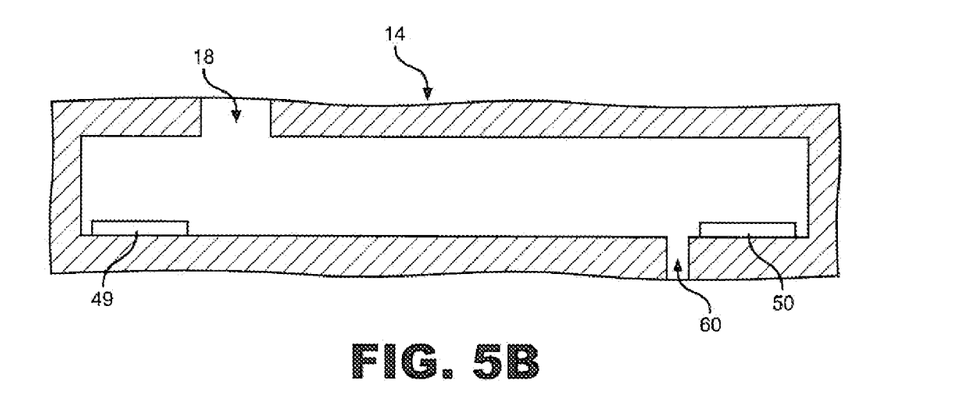
FIG. 5B depicts a second analyte chamber of the present invention including electrodes fabricated on the lower surface of the analyte chamber.
Figure 5C:
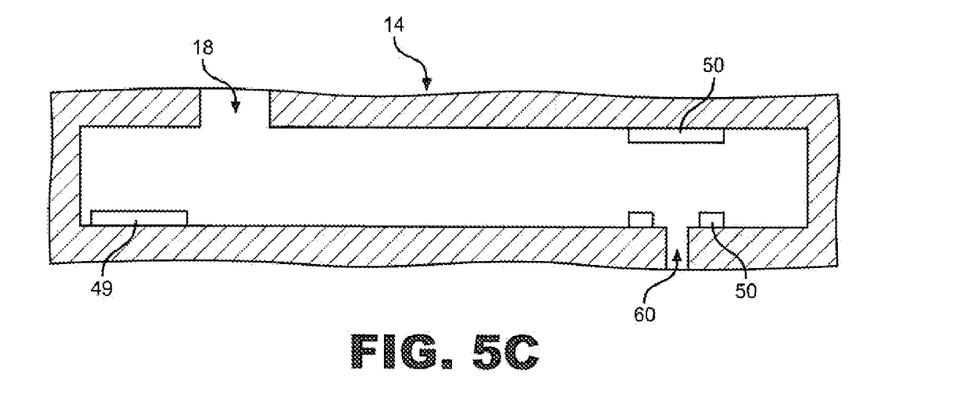
FIG. 5C depicts a third analyte chamber of the present invention including a collection electrode fabricated in two parts and located on the upper and lower surface of the analyte chamber.

Electrodes 49 and 50 used to implement the invention are shown schematically in FIG. 1 as flat plates in the opposite end planes of analyte chamber 14. For convenience, we term electrode 49 in analyte chamber 14 the source electrode and electrode 50 in interaction region 40 the collector electrode, because target molecules 44 are driven towards it. Alternatively, either or both electrodes 49 and 50 could be flat plates in the upper or lower plane (i.e., in the upper or lower surface) of analyte chamber 14, a geometry which makes them easier to fabricate but reduces the effective distance between them, as shown in FIGS. 5A and 5B respectively. In an alternative embodiment, collector electrode 50 can be implemented as a pair of flat plates located at the respective upper and lower surfaces of interaction region 40 and around nanopore 60 as shown in FIG. 5C in order to create a region of more uniform potential in the immediate vicinity of nanopore 60. In all cases, electrodes 49 and 50 can be thin films. The electrode material can be silver/silver chloride (Ag/AgCl) to provide a low impedance resistive coupling to the electrolyte solution, or an inert metal such as platinum (Pt) or tantalum (Ta) with a tantalum pentoxide ($Ta_2O_5$) surface, both of which would provide a predominantly capacitive coupling. A yet further refinement is to couple electrodes 49 and 50 to electrolyte solution in analyte chamber 14 by small salt bridges (not shown). Such bridges enable electrodes 49 and 50 to be located within a larger fluid volume, thereby reducing their impedance and self noise and increasing their lifetime.

Figure 6:
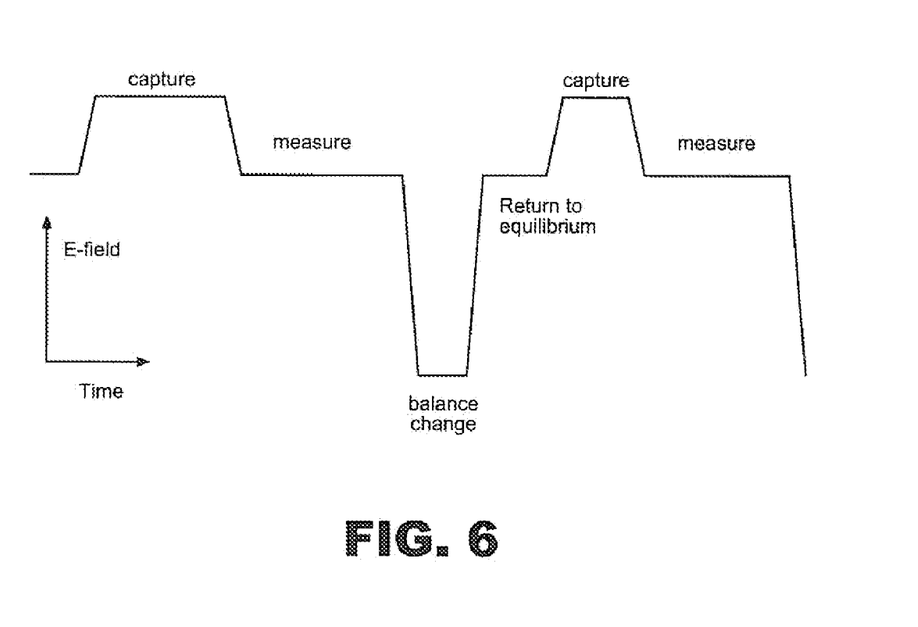
FIG. 6 is a graph of an electric field applied over time to electrodes in the sensing system of FIG. 1 in accordance with a method of the present invention.

Electrodes of inert metals such as Pt or Ta do not react chemically with the electrolyte solution, thereby allowing longer operating lifetime than Ag/AgCl electrodes. However, the operating lifetime of a resistive electrode of Ag/AgCl can be increased by reversing the direction of the electrophoretic field within system 10 such that the total charge transferred over one complete cycle of operation is zero. A possible profile of the electric field applied by a resistive electrode to the electrolyte solution over time is shown in FIG. 6. The electric field is applied to increase the number of target molecules 44 at interaction region 40 until a capture event occurs, e.g., a target molecule 44 enters a channel or a protein pore. After capture occurs, it is not necessary to keep the electric field on and the electric field can be reduced to zero while a target molecule 44 of sample 22 is measured (e.g., sequenced) using nanopore 60. During the measurement period, or at the end of it, the applied electric field can be reversed in order to balance the charge transferred between the resistive electrodes. The amplitude of the reversed field can be different from the forward direction if required. For a purely capacitive electrode, the electrophoretic force can only be applied while the voltage applied across the electrodes is changing. Thus, to create a DC potential in analyte chamber 14 it is necessary to apply a linearly increasing voltage across electrodes 49 and 50.

The increased number of target molecules 44 in interaction region 40 is a balance between the effect of electrophoresis on target molecules 44 (e.g., DNA) and diffusion of target molecules 44. If we apply an electric field E to a solution, a charged analyte will achieve a velocity, v, given by v=µE, where µ is the mobility of the analyte in the solution. When system 10 reaches equilibrium, the flux of DNA must be zero everywhere, so the electrophoretic velocity, v, must be exactly balanced by the diffusive velocity. This state of equilibrium is represented by the equation below, in which D is the diffusion constant and n is the local number of target molecules 44 per unit volume of the analyte.

$$D\frac{\partial n}{\partial x} = -vn \qquad [1]$$

The solution of equation 1 is a simple exponential with a length scale given by $l_d=D/v$:

$$n=Ae^{-x/l_d} \qquad [2]$$

If the length of the analyte chamber is L, and the initial number of analyte target molecules 44 per unit volume is $n_0$, the equilibrium value of n at a distance x away from the concentrating electrode 50 along the long axis of the analyte chamber is given by:

$$n = n_0 \frac{L}{l_d} \frac{e^{-x/l_d}}{1 - e^{-L/l_d}} \qquad [3]$$

The voltage V required to increase n by an enhancement factor of $\beta$ is given by:

$$V = \frac{\beta D}{\mu} \qquad [4]$$

In a first example, a single strand DNA molecule of order 100 bases long has a diffusion constant D of $10^{-7}$ cm$^2$/s and a mobility $\mu$ of $10^{-4}$ cm$^2$/Vs. For a 100 times increase in n (i.e. $\beta$=100) V=100 mV. The time, $\tau_d$, to drive the molecules into the interaction region such that the maximum value of n is increased by a factor $\beta$ is approximately given by:

$$\tau_d = \frac{L^2}{\beta D} = \frac{L^2}{V\mu} \qquad [5]$$

For n to return to an equilibrium distribution under the influence of diffusion over a spatial region of extent r, is given by:

$$\tau = \frac{r^2}{2D} \qquad [6]$$

Figure 7:
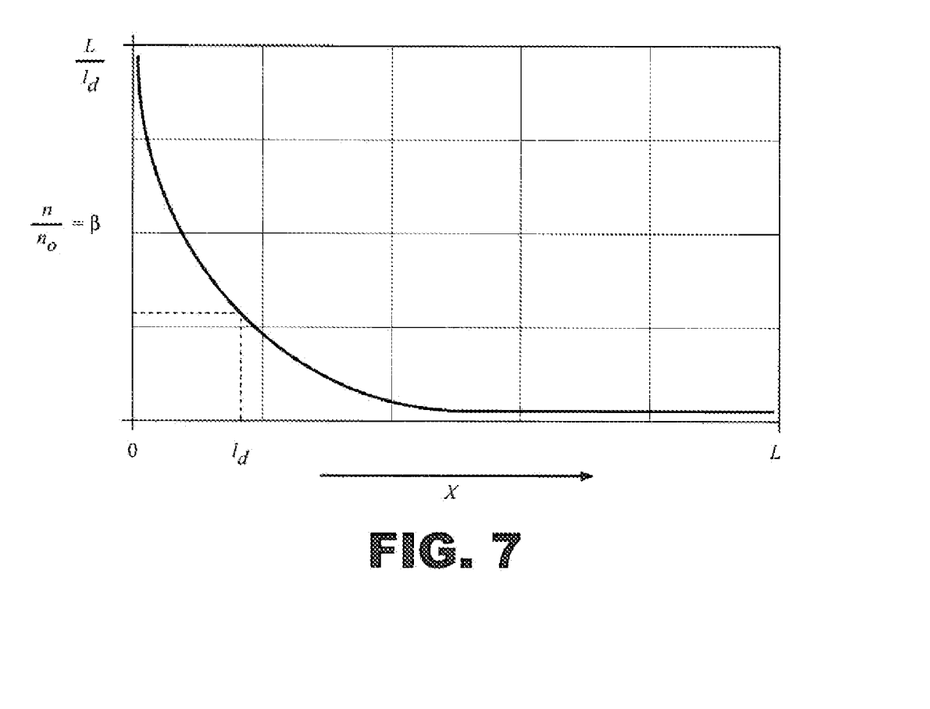
FIG. 7 is a graph depicting the local number of analyte molecules versus the distance of the analyte molecules from a collecting electrode in the system of FIG. 1.

Equation 3 shows that the increase in density of target molecules 44 is approximately equal to $L/l_d$. Thus, to increase the number of target molecules n by a factor of 100, the length L of analyte chamber 14 must be approximately 100 times $l_d$. FIG. 7 shows a plot of the number of target molecules n vs the distance x away from concentrating electrode 50. As can be seen from the graph, nanopore 60 should be located within a distance of order $l_d$ from collecting electrode 50 (x=0). Similarly, an effective length L' of interaction region 40 is of order $2l_d$. The length scale $l_d$ can be expressed in terms of the driving voltage V and the length L by:

$$l_d = \frac{DL}{\mu V} = \frac{L}{\beta} \qquad [6]$$

It is preferable that the overall volume of analyte chamber 14 be small in order to minimize the volume of sample solution 22 that must be injected into analyte chamber 14. Accordingly, in order to be within the capabilities of microfluidic system fabrication, order $l_d$ should be set in the range of about 10 μm to 100 μm and more preferably less than 10 μm. A reasonable enhancement factor $\beta$ is 100 to 1000, and this sets the range for L from about 100 μm to 10 cm, and preferably 100 μm to 1 cm. The width $W_1$ (depicted in FIG. 1) and height H (depicted in FIG. 4) of analyte chamber 14 should be as small as possible consistent with the chosen system fabrication technologies. Preferably, the width $W_1$ is less than about 1 mm and more preferably less than about 100 μm. The height H is preferably less than about 100 μm and more preferably less than about 20 μm. The width $W_1$ and height H of interaction region 40 can be the same as the main body of analyte chamber 14, or interaction region 40 can be tapered to a smaller width $W_2$ as depicted in FIG. 1 to provide a further increase in $\beta$, wherein the increase in $\beta$ is approximately the ratio of the width $W_1$ of analyte chamber 14 to the width $W_2$ of interaction region 40.

For the DNA parameters given above, and an enhancement factor $\beta$ of 100, a driving voltage of 0.1 V is required. This voltage is compatible with available electrode materials such as Ag/AgCl. Preferably, V is in the range 10 mV to 1 V. For V=0.1V and the same DNA parameters, the driving time $\tau_d$ is 1000 seconds. The time, $\tau_2$, for molecules 44 driven to the exponential distribution shown in FIG. 7 to equilibrate over the region around nanopore 60 such that they are almost all still in within interaction region 40 is of order $(l_d)^2/2D$=25 seconds for $l_d$=20 μm. In contrast, the time, $\tau_2$, for molecules 44 to diffuse out of interaction region 40 and return to their equilibrium distribution prior to application of the driving field is of order $L^2/2D$. Thus, in accordance with the present invention, a preferred approach is to drive molecules 44 to interaction region 40 with a high voltage that reduces the time $\tau_d$ but also reduces the characteristic length $l_d$ and then allow molecules 44 to distribute about nanopore 60 under the effect of diffusion. In one example, V is set to 1 V $\tau_d$=100 seconds, $l_d$=2 μm (for L=2 mm) and $\beta$=1000. If nanopore 60 is 20 μm from collector electrode 50, then $\tau_2$=25 seconds, thereby achieving a high value of n (~$50n_0$) at nanopore 60 in a time of order 125 seconds. The characteristic time $\tau_1$ for this high value of n to return to $n_0$ is of order 100,000 seconds, allowing a significant time for nanopore 60 to operate with an increased number of target molecules 44 in its vicinity. If nanopore 60 is fabricated within 1 μm of collector electrode 50 and L reduced to 100 μm, then in the example above (V=1V), $\tau_d$ is reduced to =0.25 seconds, $\tau_2$=0.06 seconds and $\tau_1$=500 seconds.

Figure 8:
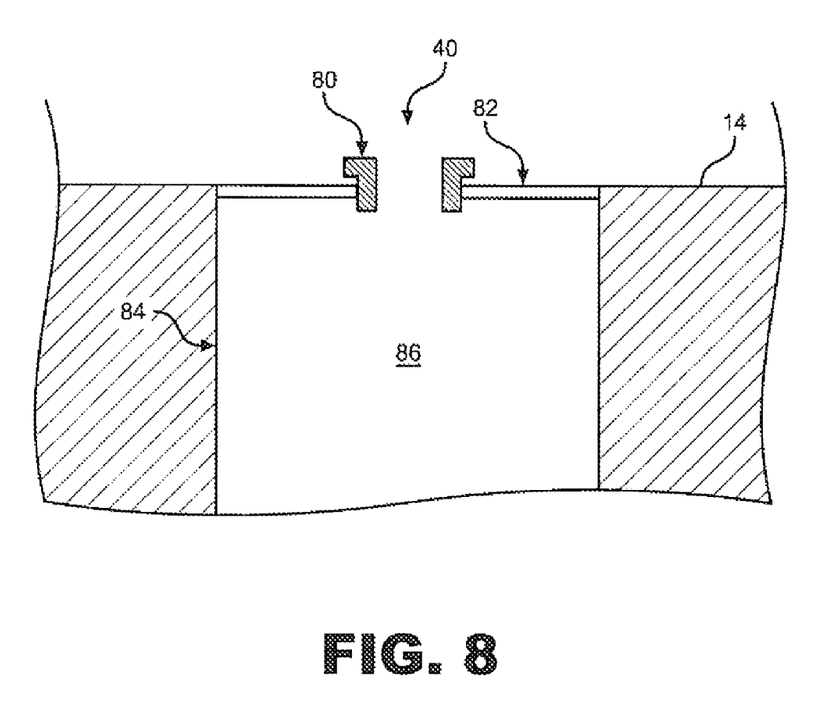
FIG. 8 is a cross-sectional side view of a nanopore of the present invention including a protein pore within a lipid bilayer.

A method for utilizing system 10 to sequence a single DNA molecule in accordance with the present invention will now be discussed with reference to FIGS. 1 and 8. In a preferred embodiment for sequencing single DNA molecules, a nanopore is comprised of a protein pore 80, or a modified ion channel, or equivalent biological structure (termed henceforth a protein pore) embedded in a lipid bilayer 82 over an orifice 84 connecting interaction region 40 with a second fluid volume 86 as shown in FIG. 8. Orifice 84 has appropriate surface properties to form an electrical seal to the bilayer as known to those skilled in the art. Orifice 84 is generally circular with a diameter of order 10 μm and preferably less than 1 μm.

Alternatively, nanopore 60 may comprise a channel 66 in the substrate of analyte chamber 14, as depicted in FIG. 2B, having a diameter of order 2 nm. In a manner known in the art, nanopore 60 can be sized such that target molecule 44 produces a measurable blocking signal when present within nanopore 60. The measured blocking signal can be utilized to sequence the monomers of a polymer, such as DNA.

In the preferred embodiment, the lipid needed to form bilayer 82 is transported to orifice 84 via a fluid input channel 90 that intersects interaction region 40 as shown in FIG. 1. In use, one or more protein pores are introduced into interaction region 40 by channel 90, and are subsequently incorporated into lipid bilayer 82 extending across orifice 84 in a manner known to those skilled in the art. It is important to note that, whereas the quantity of sample 22 is limited and must be carefully preserved, the lipid and the protein pores are relatively plentiful and the solutions containing them can be transported through microfluidic vales and channels fabricated by standard methods known to those familiar in the art.

To allow pressure release during the introduction of sample 22 and lipid and protein pore solutions to analyte chamber 14, an exit channel 92 is also provided to intersect interaction region 40. Exit channel 92 can be in the same plane as input channel 90 and may be oriented above or below it. To prevent target molecules 44 from diffusing into fluid channel 90 and exit channel 92, first and second blocking electrodes 94 and 95 are incorporated in system 10 and biased at the same voltage as between the source and collector electrodes 49 and 50. In the preferred embodiment, the voltage V of collector electrode 50 is set to 0, the electrical system circuit ground. The voltage of the source electrode 49 and blocking electrodes 94 and 95 is then set to the same positive voltage so that DNA is driven toward collector electrode 50.

To prepare system 10 to receive and measure sample 22, input port 18 is opened and a buffer solution is passed through fluid channel 90 to fill interaction region 40 and analyte chamber 14. Input port 18 is then closed to prevent further fluid flow from interaction region 40 into analyte chamber 14 during subsequent steps. A solution containing the lipid needed to form the lipid bilayer (not shown) is then inserted via input channel 90, which pushes the buffer solution that is present in interaction region 40 out through exit channel 92. Once the bilayer is formed, a second solution containing the protein pores is input into interaction region 40 by the same process. Once one or more of the protein pores have inserted into the bilayer, the solution containing the remaining protein pores is replace by buffer via input line 90, and flushed out through exit channel 92. System 10 is now ready to receive sample 22.

In a preferred embodiment, input port 18 is opened and accessed by an automated sample dispensing system indicated at 98. To minimize the amount of sample lost by dead volume, dispensing system 98 is preferably a robotic pipetter which draws in all or part of the initial sample 22 into a pipette and dispenses, sample 22 into system 10. Exit line 92 is open while sample 22 is dispensed to provide a path for displaced buffer in analyte chamber 14 to exit. Owing to the small size of analyte chamber 14, sample 22 passes into chamber 14 by a process of plug flow. That is, sample 22 is dispensed into analyte chamber 14 and slowly displaces some of the buffer in analyte chamber 14, which exits through channel 92 with minimal turbulence and mixing of sample 22 with the buffer. Once sample 22 is loaded into system 10, a voltage is applied to electrodes 49 and 50, causing an electric field between electrode 49 and 50 that drives target molecules 44 towards electrode 50. The arrival and subsequent interaction of target molecules 44 with nanopore 60 is monitored using a current sensor 100 as known to those skilled in the art combined with electrodes 74 and 75, or 74 and one of 49 or 50. When sufficient data has been collected, input port 18 is opened and new buffer solution is introduced into analyte chamber 14 to prepare system 10 for a new sample. As part of preparing system 10, the bilayer can be broken and remade with a new protein pore, or can be left intact, as desired.

Figure 9:
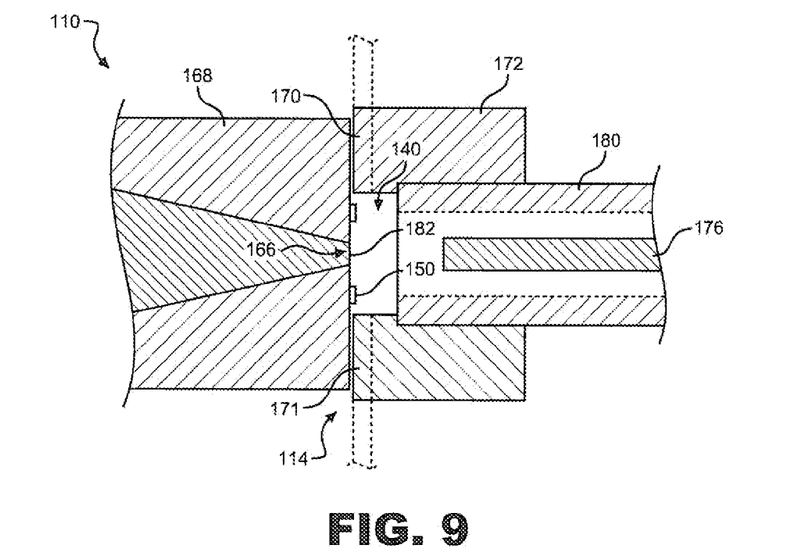
FIG. 9 a is a partial cross-sectional side view of an alternative embodiment of the interaction region of the present invention.
Figure 10A:
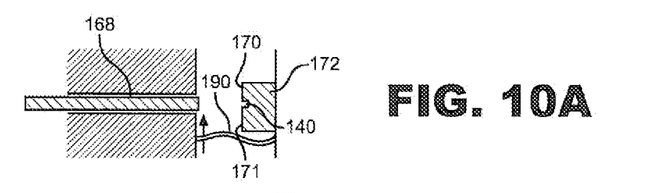
FIG. 10A is a partial cross-sectional side view of the system of FIG. 9, depicting the introduction of a lipid bilayer across the opening of a capillary.
Figure 10B:
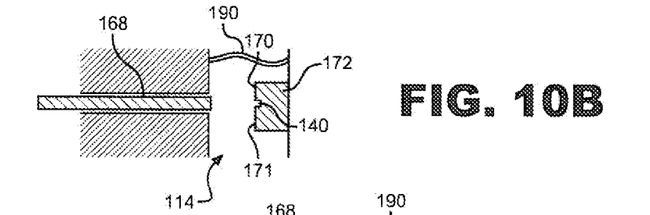
FIG. 10B is a partial cross-sectional side view of the system of FIG. 9, depicting the system after the introduction of the lipid bilayer.

In an alternate embodiment, a bilayer is formed over an orifice in bulk solution and then interfaced to interaction region 40 after it is formed. This approach enables greater flexibility in the way the bilayer is formed, rather than limiting its formation to those processes compatible with the very small volume of interaction region 40. Similarly, the protein pore can be incorporated into the bilayer before the bilayer is interfaced to interaction region 40. An alternative sensing system configuration 110 depicted in FIGS. 9-11 enables the bilayer to be formed and the protein pore inserted in this way. With initial reference to FIG. 9, a cross-sectional side view of an analyte chamber 114 is depicted, which shows an interaction region 140 adjacent an orifice 166 formed in a glass or quartz substrate capillary 168 (i.e., a first portion of analyte chamber 114). In this embodiment, interaction region 140 is formed as a channel defined between first and second end walls 170 and 171 of a substrate 172 (i.e., a second portion of analyte chamber 114), with one side of the channel open. A first circular electrode 150 is formed around orifice 166 in an end plane of substrate 168. Electrode 150 provides the same function as electrode 50 in system configuration 10 depicted in FIG. 1. In system 110, an electrode 149 shown in FIG. 11 is equivalent to source electrode 49 in FIG. 1. To provide an electrical connection with low electrical noise, a separate electrode 176 inside a capillary 180 can be used to provide a bias voltage and current across a protein pore with a counter electrode (not shown) inside capillary 168. Capillary 180 is preferably in the form of 500 μm polyimide tubing including 3-6 M sodium chloride agar (i.e., a salt bridge). For clarity, capillary 180 and electrode 176 are not shown in FIGS. 10A-10C.

Figure 10C:
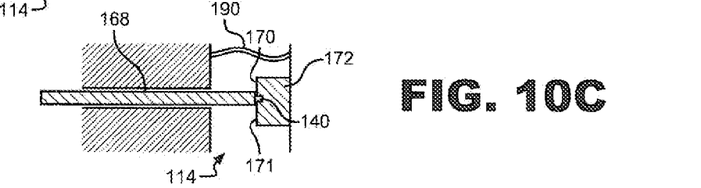
FIG. 10C is a partial cross-sectional side view of the system of FIG. 9, depicting the capillary abutting an analyte chamber to define an interactive region.
Figure 11:
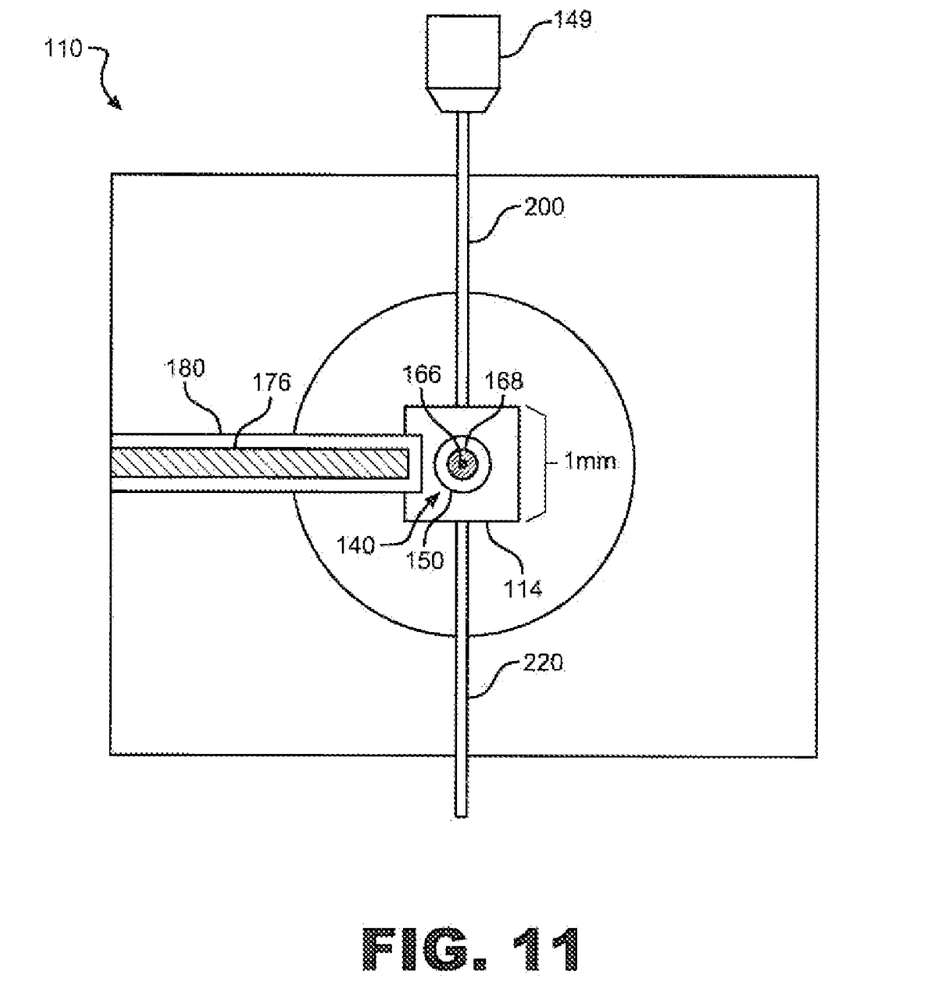
FIG. 11 is an end view of the system of FIG. 9.

As depicted in FIGS. 9 and 10A-10C, in order to form a lipid bilayer 182, orifice 166 (not depicted in FIGS. 10A-10C) is exposed to a solution 190 containing lipids by raising the fluid level of solution 190 from below orifice 166 to above orifice 166 in order to form a bilayer across orifice 166 in a manner known in the art. A protein pore (not shown) is inserted into the lipid bilayer 182 by exposing it to a solution containing the protein until an incorporation of the protein pore in lipid bilayer 182 is detected by a current sensor (not shown). The lipid and protein pore solutions are flushed to minimize contamination in interaction region 140 and then substrate 168 is pushed against end walls 170 and 171, as shown in FIG. 10C, to complete interaction region 140. In other words, the first portion of analyte chamber 114 is adapted to be positioned relative to the second portion of analyte chamber 114 such that the first portion of the analyte chamber, including the nanopore, can be selectively connected and disconnected from interaction region 140. The interaction region 140 preferably has a volume of approximately 1 μl.

Once bilayer 182 is formed and the protein pore inserted, the sample is introduced into an input line 200 shown in FIG. 11, and flows into interaction region 140 by plug flow in the same manner described above with respect to system 10. That is, as a sample is introduced through input line 200, buffer is pushed out through exit line 220. In a preferred embodiment, input line 200 and exit line 220 constitute capillaries having a diameter of approximately 25 μm.

An important feature of the invention is that, in contrast to using a preprocessing step in which the sample is preconcentrated by a centrifuge or equivalent method, increasing the target molecular density at the detection element (e.g., nanopore) by the method described by the invention does not reduce the volume of original sample solution. Maintaining the sample volume facilitates dividing the sample into multiple parallel measurement systems thereby allowing an increased overall rate of molecular analysis. Accordingly, it is a particular feature of the invention that it can be embodied as a parallel set of individually accessed measurement units. Such a system of units could be filled serially by a simple robotic pipetting system. In contrast, when the original sample is reduced in volume, the volume of the analyte chamber in the subsequent measurement system must be reduced in proportion, thereby making the development of an array of interrogation elements in the reduced volume more technically challenging and more costly.

In summary, increasing the number of analyte molecules in the immediate vicinity of a nanopore or equivalent single molecule interrogation system provides an increased interaction rate with the interrogation system. This in situ method reduces or eliminates the need to preconcentrate the sample, thereby preserving the initial sample volume and facilitating the use of multiple measurement system in parallel. The system has many applications, and in particular when applied to sequencing a biopolymer via a nanopore it has the potential to revolutionize the DNA sequencing process by removing the costly and time consuming preliminary steps of amplifying and or concentration the initial DNA sample.

Although described with reference to preferred embodiments of the present invention, it should be readily understood that various changes and/or modification can be made to the invention without departing from the spirit thereof. For example, although particularly useful for singe molecule DNA sequencing, the invention also applies to the general case of increasing the arrival rate of single molecules at a nanopore. The important point is that the invention draws individual molecules from solution to a region so small that the addition of the molecules into that region has a substantial effect on the subsequent interrogation of the molecules. For example, the capture rate of molecules or particles by a nanopore is limited by the arrival rate of individual molecules at the nanopore opening. As a second example, the region could contain a number of discrete single molecule recognition sites such that the arrival of each molecule can be distinguished. In general, the invention is only intended to be limited by the scope of the following claims.

We claim:

1. An electrolytic system for increasing nanopore and molecule interactions comprising:
   an analyte chamber having a length L adapted to contain a sample solution, the analyte chamber including an access port for introduction of fluids into the analyte chamber;
   at least one nanopore formed in the analyte chamber within an interaction region, the at least one nanopore includes first and second opposing sides; and
   first and second electrodes, both arranged on the first side of the at least one nanopore within the analyte chamber, adapted to create an electric field along the length L of the analyte chamber to drive molecules of interest toward the interaction region; third and fourth electrodes located on the first and second opposing sides of the nanopore respectively, wherein actuation of the first and second electrodes is adapted to increase an arrival rate of molecules of interest to the first side of the nanopore wherein the third and fourth electrodes are adapted to apply an electric field across the nanopore to drive one of the molecules of interest into the nanopore.

2. The system of claim 1, wherein the voltage applied to the first and second electrodes directs the molecules of interest in a first direction leading to the interaction region and the voltage to the third and fourth electrodes directs the molecules of interest in a second direction after reaching the interaction region, with the second direction being distinct from the first direction.

3. The system of claim 2, wherein the second direction is substantially perpendicular to the first direction.

4. The system of claim 1, further comprising:
   a sensor adapted to detect an event wherein one of the molecules of interest interacts with the nanopore, wherein the system is adapted to count, discriminate or characterize the one of the molecules of interest.

5. The system of claim 4, wherein the system is adapted to identify individual polymers or units of a polymer.

6. The system of claim 4, wherein the system is adapted to sequence a biopolymer.

7. The system of claim 1, wherein the nanopore is located at a distance $l_d$ from the second electrode along the length L of the analyte chamber, and distance $l_d$ is approximately L/100.

8. The system of claim 7, wherein $l_d$ is less than approximately 100 μm.

9. The system of claim 8, wherein $l_d$ is less than approximately 10 μm.

10. The system of claim 1, wherein L is from about 100 μm to 1 cm.

11. The system of claim 1, wherein each of a height and a width of the analyte chamber is in the order of L/100 or less.

12. The system of claim 1, wherein a width of the interaction region is less than a width of the analyte chamber.

13. The system of claim 1, wherein the first and second electrodes are silver/silver chloride electrodes.

14. The system of claim 1, wherein the first and second electrodes are selected to be electrochemically unreactive with the electrolyte.

15. The system of claim 1, wherein the nanopore is selected from the group consisting of a protein pore, an ion channel and a modified ion channel.

16. The system of claim 15 wherein the nanopore is a protein pore extending through a lipid bilayer.

17. The system of claim 1, wherein the analyte chamber further comprises a fluid input channel and an exit channel, each of the fluid input and fluid exit channels intersecting the interaction region.

18. The system of claim 1, wherein the nanopore is located at a first portion of the analyte chamber adapted to be positioned relative to a second portion of the analyte chamber defining the interaction region, such that the first portion of the analyte chamber can be selectively connected and disconnected from the interaction region.

19. A method, for increasing nanopore and molecule interactions comprising:
   providing a nanopore at an interactive region within a first analyte chamber, with the nanopore including first and second opposing sides;
   introducing a sample solution to the first analyte chamber through an access port, the sample solution containing a molecule of interest; and
   applying a voltage to first and second driving electrodes, both arranged on the first side of the nanopore within the first analyte chamber, to produce an electric field to drive the molecule of interest from the access port to the interactive region to increase the number of target molecules within the interactive region for interaction with the nanopore.

20. The method of claim 19, further comprising:
   detecting the event utilizing a current sensor; and
   characterizing the molecule of interest.

21. The method of claim 20, wherein the molecule of interest is a biopolymer and characterizing the molecule of interest, comprises determining the sequence of the biopolymer.

22. The method of claim 19, wherein providing the nanopore at the interactive region within the first analyte chamber constitutes the steps of:
  introducing a buffer solution to the fast analyte chamber;
  introducing a lipid solution to the first analyte chamber at the interaction region to form a lipid bilayer;
  introducing a protein pore solution to the first analyte chamber at the interaction region to form a lipid bilayer containing a protein pore; and
  introducing a buffer solution to the first analyte chamber to flush out the protein pore solution through an exit channel of the first analyte chamber.

23. The method of claim 19, further comprising:
  dividing the sample solution into subsamples containing the molecule of interest, wherein introducing the sample solution to the first analyte chamber through the access port constitutes adding one of the subsamples to the analyte chamber;
  providing a nanopore at an interactive region within a second analyte chamber;
  introducing one of the subsamples to the second analyte chamber through an access port of the second analyte chamber;
  applying a voltage to first and second driving electrodes of the second analyte chamber to produce an electric field to drive the molecule of interest from the access port of the second analyte chamber to the interactive region of the second analyte chamber to increase the probability of an event wherein the molecule of interest interacts with the nanopore of the second analyte chamber;
  detecting the interaction of the molecule of interest with the nanopore of the first analyte chamber;
  detecting the interaction of the molecule of interest with the nanopore of the second analyte chamber; and
  characterizing the molecule of interest, wherein the rate of characterizing the molecule of interest is increased due to the use of multiple analyte chambers.

24. The method of claim 19, wherein the voltage applied is between 10-1000 millivolts.

25. The method of claim 19, the method further comprising:
  applying a voltage to first and second blocking electrodes to produce an electric field which prevents the molecule of interest from migrating from the interactive region into either a fluid input channel or a fluid exit channel of the analyte chamber.

26. A method for increasing nanopore and molecule interactions comprising:
  providing a nanopore at an interactive region within a first analyte chamber, with the nanopore including first and second opposing sides;
  introducing a sample solution to the first analyte chamber through an access port, the sample solution containing a molecule of interest; and
  applying a voltage to first and second driving electrodes, both arranged on the first side of the nanopore within the first analyte chamber to produce an electric field to drive the molecule of interest from the access port to the interactive region to increase the probability of an event wherein the molecule of interest interacts with the nanopore, and
  applying a voltage to third and fourth electrodes located on the first and second opposing sides of the nanopores respectively to produce an electric field across the nanopore.

27. The method of claim 26, wherein the voltage applied to the first and second driving electrodes directs the molecule of interest in a first direction leading to the interactive region and the voltage to the third and fourth driving electrodes directs the molecule of interest in a second direction after reaching the interactive region, with the second direction being distinct from the first direction.

28. The method of claim 27, wherein the second direction is substantially perpendicular to the first direction.

29. The method of claim 27, wherein the voltage applied to the first and second driving electrodes is greater than the voltage applied to the third and fourth driving electrodes.

* * * * *